US00PP20280P2

(12) United States Plant Patent
Blew

(10) Patent No.: US PP20,280 P2
(45) Date of Patent: Sep. 8, 2009

(54) ***GAZANIA* PLANT NAMED 'TANGERINE FROST'**

(50) Latin Name: *Gazania linearis*
Varietal Denomination: Tangerine Frost

(75) Inventor: Robert Blew, Bridgeton, NJ (US)

(73) Assignee: Centerton Nursery, Inc., Bridgeton, NJ (US)

( * ) Notice: Subject to any disclaimer, the term of this patent is extended or adjusted under 35 U.S.C. 154(b) by 0 days.

(21) Appl. No.: 12/073,132

(22) Filed: Feb. 29, 2008

(51) Int. Cl.
*A01H 5/00* (2006.01)

(52) U.S. Cl. ..... Plt./334
(58) Field of Classification Search ..... Plt./334
See application file for complete search history.

*Primary Examiner*—Susan B McCormick Ewoldt
(74) *Attorney, Agent, or Firm*—Buchanan Ingersoll & Rooney PC

(57) ABSTRACT

A new and distinct *Gazania linearis* perennial cultivar of the semi-evergreen type is provided. The new cultivar forms attractive daisy-like blossoms of good substance having petals which are rich orange with yellow tips on the upper surface. In U.S.D.A. Hardiness Zone No. 6, blooming commonly begins during May and commonly ends during mid-September. Attractive dark green foliage having pubescence on the under surface is formed. A propensity to readily produce new crown tissue is displayed. The winter hardiness is good. The new cultivar is well suited for growing as distinctive colorful ornamentation in the landscape.

6 Drawing Sheets

Figure 1:
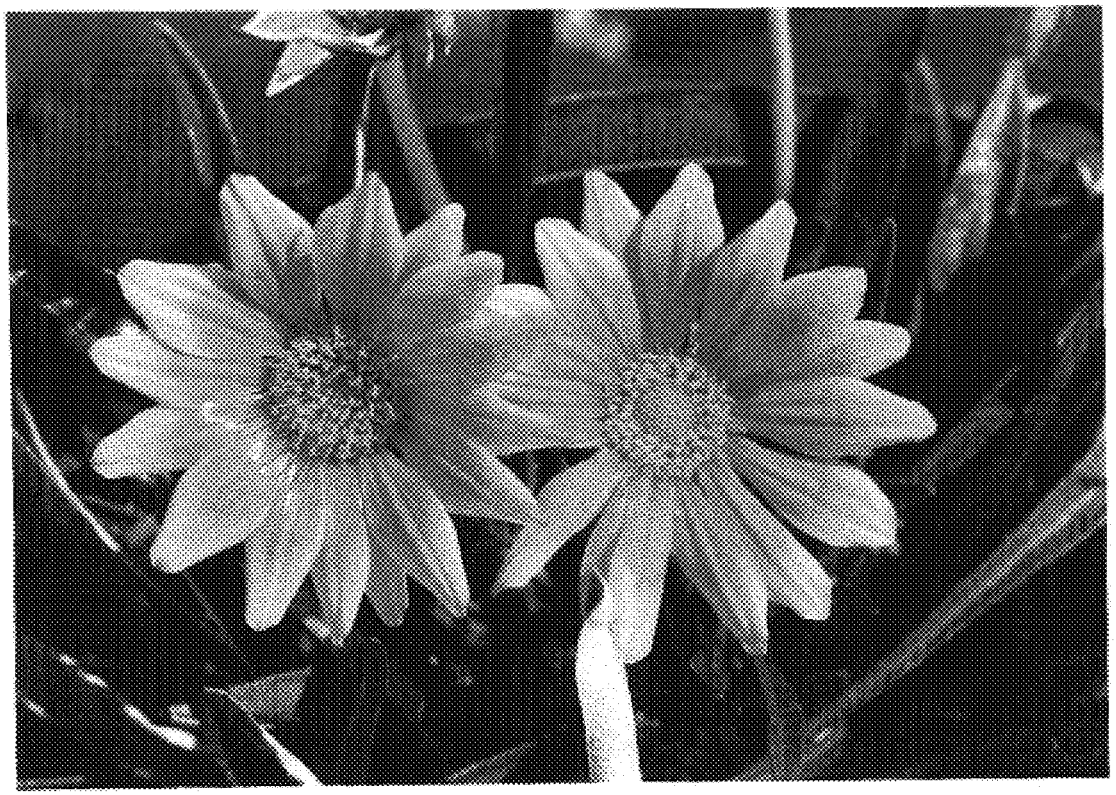

Botanical/commercial classification: *Gazania linearis*/ Treasure Flower.
Varietal denomination: cv. Tangerine Frost.

SUMMARY OF THE INVENTION

The present invention comprises a new and distinct cultivar of *Gazania* plant and hereinafter is referred to by the cultivar name 'Tangerine Frost'. *Gazania* plants are members of the Asteraceae Family, and are commonly grown as an ornamental perennial which forms daisy-like blossoms.

The new cultivar of the present invention was discovered during June, 2003, in a nursery setting at Bridgeton, N.J., U.S.A. Such new cultivar was discovered as a partial plant mutation of unknown causation on a small portion of a single plant of the 'Colorado Gold' cultivar (non-patented in the United States). The parent plant at the time of the discovery was approximately 12 to 15 months of age. Such parent plant had been started from a plug and once had been transplanted.

The discoverer was attracted to the new cultivar primarily in view of its distinctive blossom coloration which differed from that of the parent 'Colorado Gold' cultivar and all other *Gazania* cultivars of which the discoverer was aware. The new plant of the present invention following its discovery has been carefully maintained and evaluated.

It was found that the new *Gazania* plant possesses the following combination of characteristics:

(a) forms attractive rich orange daisy-like blossoms of good substance bearing petals which on the upper surface are rich orange with yellow tips, (b) displays a long blooming season with repeat blooming which commonly begins during May and ends during mid-September in U.S.D.A. Hardiness Zone No. 6, (c) displays attractive dark green semi-evergreen foliage having pubescence on the under surface, (d) exhibits a propensity to readuly produce new crown tissue, and (e) displays good winter hardiness.

The new cultivar resembles the blooming habit of its 'Colorado Gold' parent in the sense that it commonly possesses an unusually long and substantially continuous blooming season of up to approximately 120 days in U.S.D.A. Hardiness Zone No. 6. The new cultivar has been found to be hardy to at least −20° F. unlike most other species of *Gazania* which commonly are hardy to only approximately 32° F.

The new cultivar is well suited for forming attractive ornamentation when grown in parks and gardens or in pots such as on a patio. Even when not in bloom a generally eye-pleasing ground cover is provided by the dark green vegetation.

The new cultivar can be readily distinguished from the 'Colorado Gold' cultivar in view of the distinctive blossom coloration. Unlike the new 'Tangerine Frost' cultivar, the previously available 'Colorado Gold' cultivar produces yellow blossoms with small brown center markings. Also, the 'Colorado Gold' blossoms are considered to be of a partially desirable substance.

To the best of the knowledge of the originator the new 'Tangerine Frost' cultivar is the first long and substantially continuously blooming *Gazania linearis* plant having the unique blend of blossom coloration combined with good hardiness to approximately −20° F.

Asexual reproduction of the new cultivar by division was initially carried out beginning on Sep. 15, 2003 at Bridgeton, N.J., U.S.A. At the time of such asexual reproduction the original plant of the new cultivar consisted of two portions of crown tissue that were phenotypically identical to each other. More specifically, a crown portion of the new cultivar was removed from the source plant and the tissue was further divided. It has been demonstrated that the characteristics of the new cultivar are firmly fixed and are well retained following asexual reproduction.

BRIEF DESCRIPTION OF THE PHOTOGRAPHS

The accompanying photographs were prepared on Jul. 21, 2007, and show as nearly true as it is reasonably possible to make the same in color illustrations of this character, typical blossoms and foliage of the new cultivar of the present invention. The plant was being grown outdoors in pot culture at Bridgeton, N.J., U.S.A. The observed plants were either one or two years of age.

FIG. 1—illustrates a typical pair of fully opened blossoms from above wherein the rich orange petal coloration with yellow tips is shown. The upper surfaces of typical foliage are shown in the background.

Figure 2:
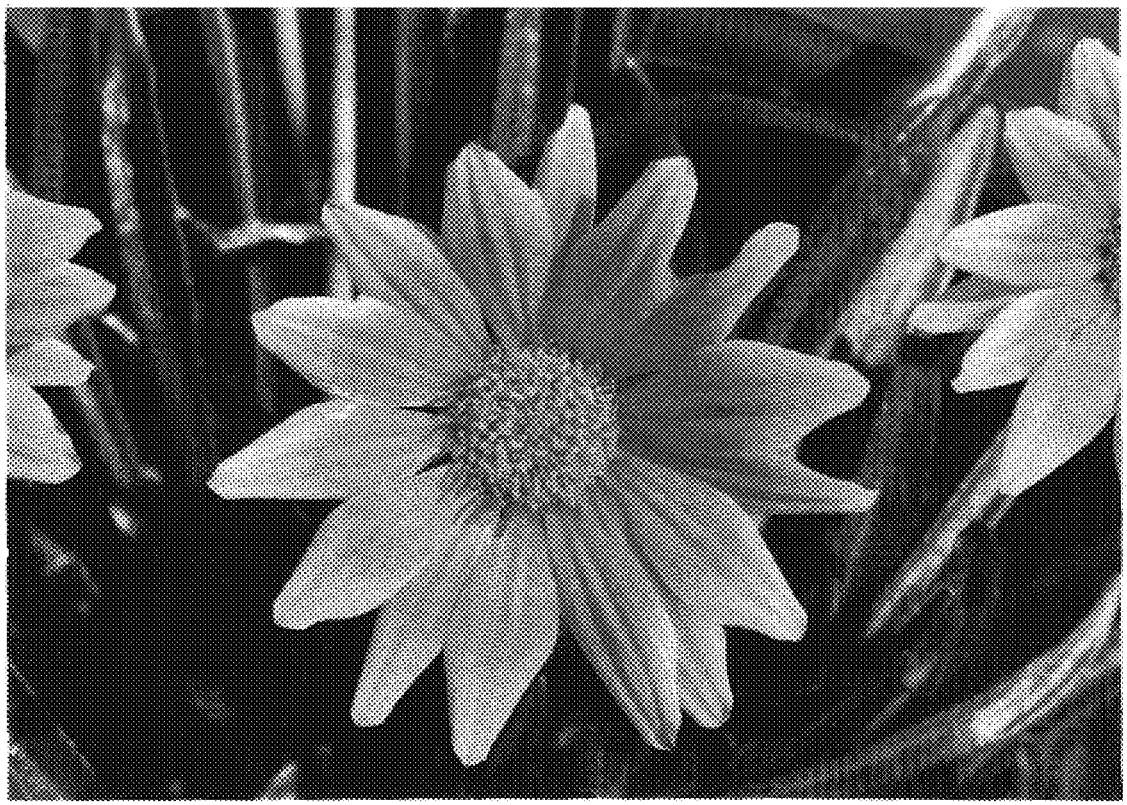

FIG. 2—illustrates a closer view from above of a typical fully opened blossom together with the upper surfaces of typical foliage in the background.

Figure 3:
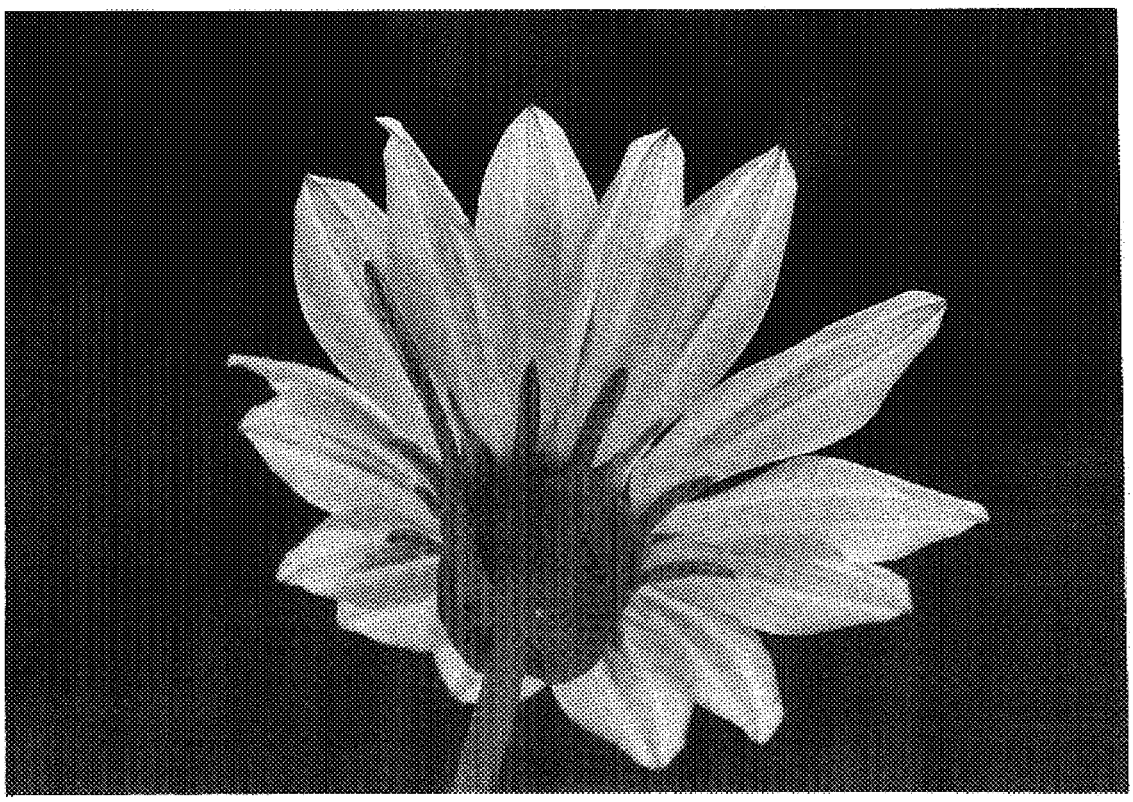

FIG. 3—illustrates a typical blossom from below wherein some darkening of the midrib coloration is shown.

Figure 4:
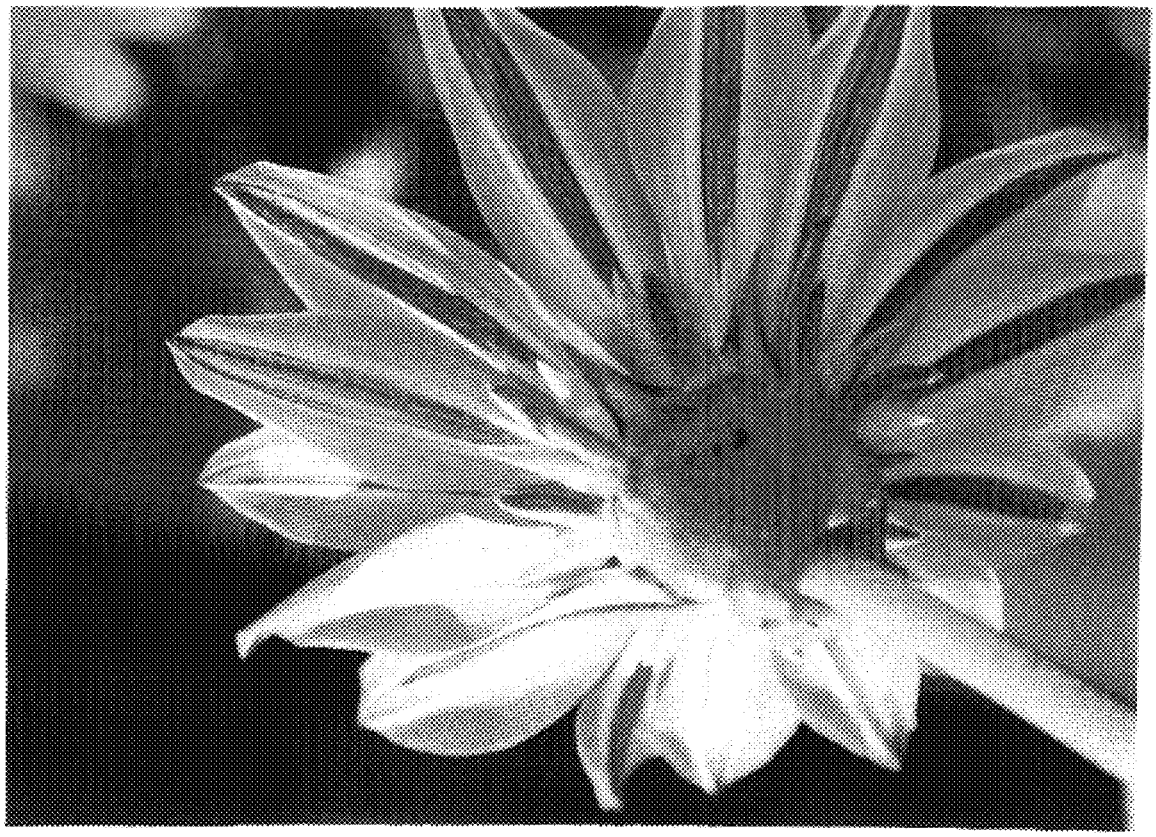

FIG. 4—illustrates a closer view of a typical blossom from below wherein the darkened coloration of midribs is more readily apparent.

Figure 5:
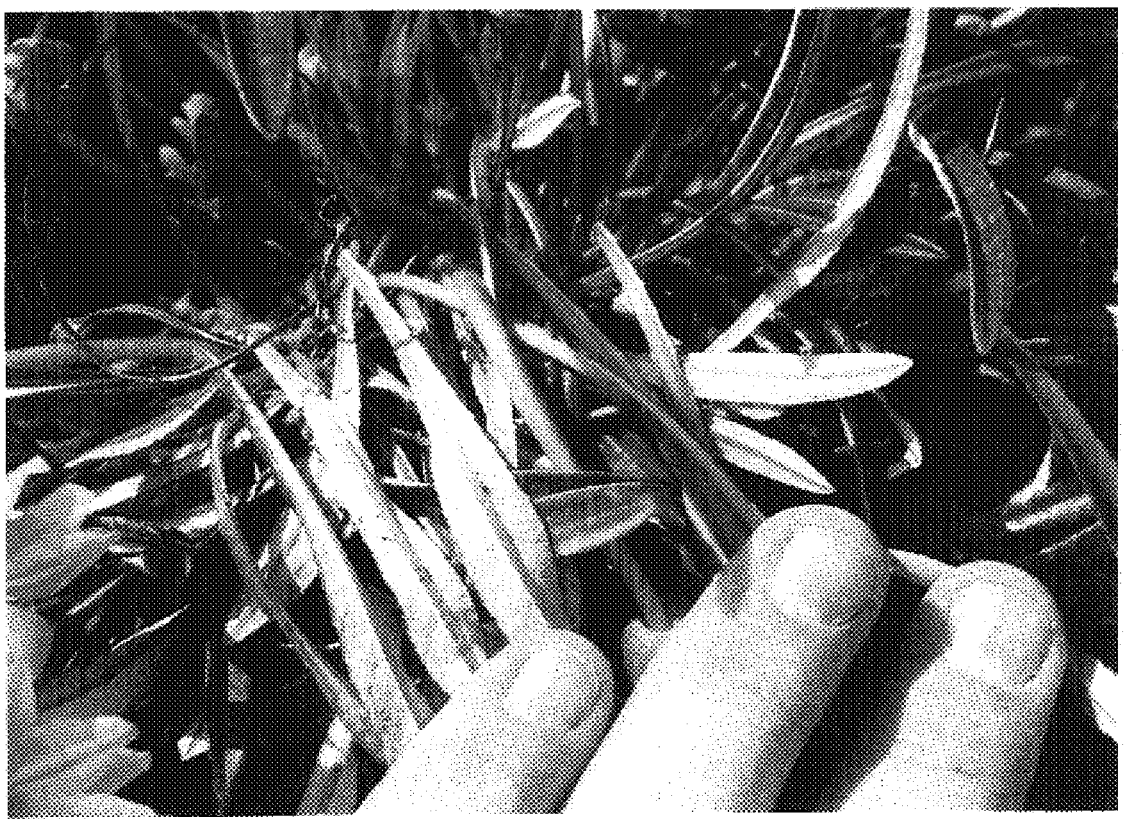

FIG. 5—illustrates the under surfaces of typical foliage where pubescence of light coloration is shown primarily at locations other than the midrib.

Figure 6:
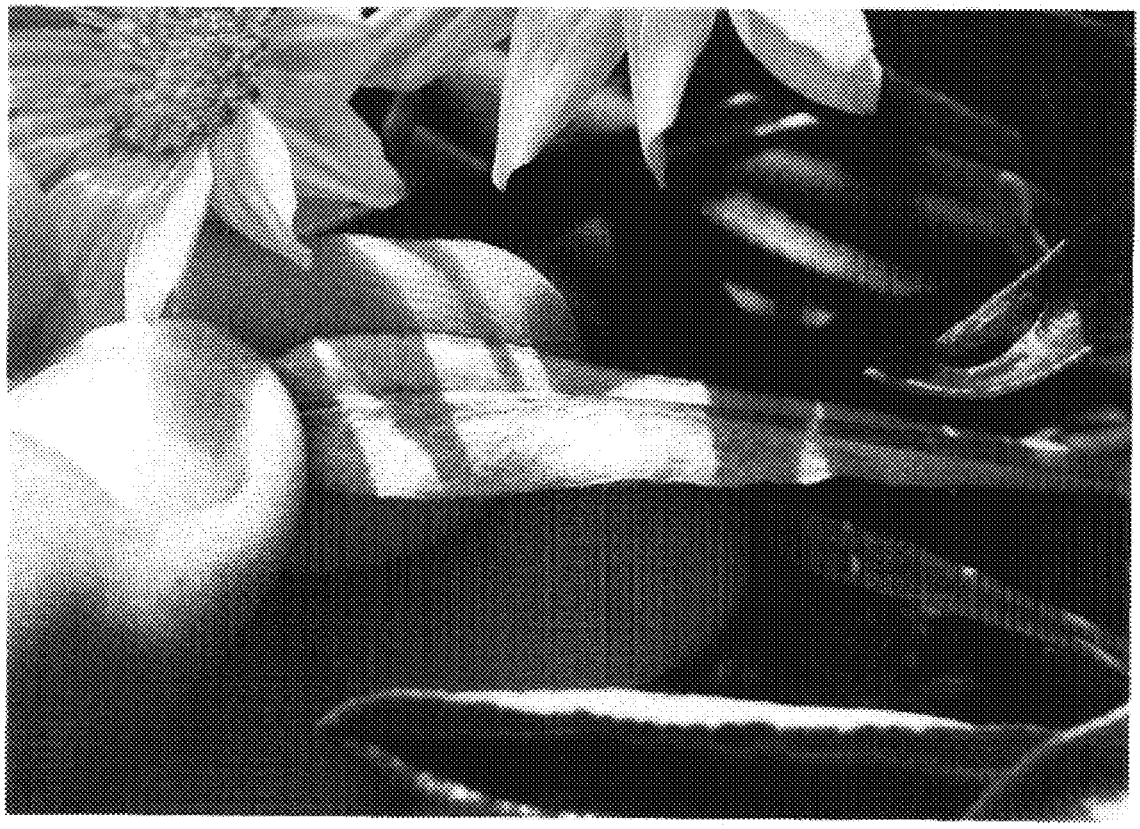

FIG. 6—illustrates at the center a close view of the under surface of a typical leaf wherein the pubescence of light coloration is shown primarily away from the midrib.

DETAILED DESCRIPTION

The chart used in the identification of the colors described herein is the R.H.S. Colour Chart of The Royal Horticultural Society, London, England. In some instances, more common color terms are provided and are to be accorded their customary dictionary significance. The plants of the new cultivar were approximately one or two years of age when observed during July, 2007 while growing at Bridgeton, N.J., U.S.A. under field growing conditions.

Plant:

*Height.*—Approximately 9 cm at an age of one year.

*Width.*—Approximately 34 cm at an age of one year.

*Foliage.*—Form: compact and mounding with leaves growing from a central crown. Quantity: abundant, with a mature plant commonly having approximately 45 leaves per plant. Leaf Size: commonly approximately 1 cm in width on average at the widest point, approximately 2 mm in width on average at the base, and approximately 11.5 cm in length on average. Leaf Shape: linear and slightly spooned. Texture: glabrous no the upper surface and pubescent on the under surface primarily away from the midrib. Color on upper surface: Green Group 139A except at base which is lighter green near Green Group 139C. Color on under surface: midrib commonly is near Green Group 139C with the pubescent remainder being near Greyed-Green Group 190D. Type: semi-evergreen with the plant commonly retaining some green coloration during the winter in U.S.D.A. Hardiness Zone No. 6b.

*Flower stems.*—Approximately 10 cm in length on average and near Yellow-Green Group 145B in coloration.

*Disease resistance.*—Typical of *Gazania linearis* with no particular disease problems having been observed to date.

Inflorescence:

*Bud.*—Form: modified oval. Size: on the day prior to opening commonly approximately 1 cm in length on average, and approximately 1.5 cm in width on average. Opening Rate: commonly approximately two hours on average. Peduncle Character: rigid and semi-sturdy. Peduncle Color: Green Group 140B.

*Flower.*—Size: commonly has a diameter of approximately 6 cm on average and a depth of approximately 3 cm on average. Borne: singly on terminals above the foliage. Petal Number: commonly 15 in an imbricated arrangement. Petal Shape: Elliptical with flat margins and an acuminate apex. Petal Length: commonly approximately 3.5 cm on average. Petal Width: commonly approximately 7.5 mm on average. Petal color on upper surface: Bicolored, generally Orange Group 25A blended to Yellow-Orange Group 14B at the tip. Petal color on under surface: Generally Orange Group 25A with some darkening commonly near Greyed-Green Group 191A at the midrib. Blooming Habit: the flowers commonly bloom substantially continuously with repeat blooming for up to approximately 120 days per year in U.S.D.A. Hardiness Zone No. 6. Effects of Weather: the flowers commonly withstand rain damage in view of the strength of the petals. Lasting Quality: commonly at least 2 to 3 days. As with other *Gazania* cultivars, the flower closes during periods of low or no sunlight and reopens at the start of a new day. As with other *Gazania* cultivars, cooler morning temperatures (e.g., 65° F.) will delay the flower opening until a higher sunlight angle is available. Fragrance: none.

*Reproductive organs.*—Androecium: very small as illustrated. Pistil Length: Approximately 5 mm on average. Pollen Color: Yellow-Orange Group 17B. Stigma Configuration: Two-parted. Stigma Color: Orange Group 25A.

*Fruit.*—Fruit and seeds have not been observed during observations to date.

Hardiness: Cold tolerance is displayed in U.S.D.A. Hardiness Zone No. 5a, and heat tolerance is displayed in U.S.D.A. Hardiness Zone No. 8b.

The 'Tangerine Frost' plant has not been observed under all possible environmental conditions to date. Accordingly, it is possible that the phenotype may vary somewhat with variations in the environment, such as temperature, light, day length, contact with pesticides, etc.

I claim:

1. A new and distinct *Gazania linearis* plant having the following combination of characteristics:

(a) forms attractive rich orange daisy-like blossoms of good substance bearing petals which on the upper surface are rich orange with yellow tips, (b) displays a long blooming season with repeat blooming which commonly begins during May and ends during mid-September in U.S.D.A. Hardiness Zone No. 6, (c) displays attractive dark green semi-evergreen foliage having pubescence on the under surface, (d) exhibits a propensity to readily produce new crown tissue, and (e) displays good winter hardiness;

substantially as illustrated and described.

* * * * *